United States Patent [19]
Didenko et al.

[11] Patent Number: 6,013,438
[45] Date of Patent: Jan. 11, 2000

[54] ASSAY FOR DETECTING APOPTOTIC CELLS

[75] Inventors: Vladimir Didenko; Peter Hornsby, both of Houston, Tex.

[73] Assignee: Baylor College of Medicine, Houston, Tex.

[21] Appl. No.: 08/758,027

[22] Filed: Nov. 27, 1996

[51] Int. Cl.$^7$ .............................. C12Q 1/68; G01N 33/53
[52] U.S. Cl. ................................. 435/6; 435/7.1
[58] Field of Search .................... 435/6, 7.1, 7.2

[56] References Cited

U.S. PATENT DOCUMENTS

| | | | |
|---|---|---|---|
| 5,330,972 | 7/1994 | Cope | 514/2 |
| 5,484,710 | 1/1996 | Reed et al. | 435/69.1 |
| 5,500,432 | 3/1996 | Nicolaou et al. | 514/281 |
| 5,512,435 | 4/1996 | Renschler et al. | 435/6 |
| 5,527,682 | 6/1996 | Owens et al. | 435/6 |
| 5,624,808 | 4/1997 | Thompson et al. | 435/7.24 |

OTHER PUBLICATIONS

J. Pathol. 170(1):1–8 (Ansari et al) 1993.
Arends, et al., American Journal of Pathology 136(3), 593–608, 1990. Apoptosis: The role of the Endonuclease.
Columbano, A., Journal of Cellular Biochemistry 58, 181–190, 1995. Cell Death: Current Difficulties in Discriminating Apoptosis from Necrosis in the Context of Pathological Processes In Vivo.
Didenko, et al., Journal of Clinical Investigation 97(7), 1723–1731, 1996. Expression of p21$^{WAFI/CIPI/SDII}$ and p53 in Apoptotic Cells in the Adrenal Cortex and Induction by Ischemia/Reperfusion Injury.
Didenko, et al., Journal of Histochemistry and Cytochemistry 44(6), 657–660, 1996.A Quantitative Luminescence Assay for Nonradioactive Nucleic Acid Probes.
Gavrieli, et al., Journal of Cell Biology 119(3), 493–502, 1992. Identifiaction of Programmed Cell Death In Situ via Specific Labelling of Nuclear DNA Fragmentation.
Grasil–Kraupp, et al., Hepatology 21, 1465–1468, 1995, In situ Detection of Fragmented DNA (TUNEL Assay) Fails to Discriminate Among Apoptosis, Necrosis, and Autolytic Cell death: A Cautionary Note.
Lutter, Nucleic Acids Research 6(1) 41–56, 1979. Precise location of DNase I cutting sites in the nucleosome core determined by high resolution gel electrophoresis.
Sasano, H., Endocrine Pathology 6(2), 87–89, 1995. In Situ End Labeling and Its Applications to the Study of Endocrine Disease: How Can We Study Programmed Cell Death in Surgical Pathology Materials.
Sollner–Webb, et al., Cell 14, 611–627, 1978. DNase I, DNase II and Staphylococcal Nuclease Cut at Different, Yet Symmetrically Located, Sites in the Nucleosome Core.
Van Lookeren Campagne, et al., European Journal of Neuroscience 7, 1627–1640, 1995. NMDA and Kainate Induce Internucleosomal DNA Cleavage Associated with Both Apoptotic and Necrotic Cell Death in the Neonatal Rat Brain.
Yang, et al., Experimental Cell Research 221, 126–131, 1995. Increased expressin of p21$^{Sdll}$ in Adrenocortical Cells When They are Placed in Culture.
Yasuda, M., et al., Archives of Histology and Cytology 58(2), 185–190, 1995. Apoptotic Cells in the Human Endometrium and Placental Villi: Pitfalls in Applying the TUNEL Method.

*Primary Examiner*—Eggerton A. Campbell
*Attorney, Agent, or Firm*—Fulbright & Jaworski L.L.P.

[57] ABSTRACT

The invention relates to the detection of apoptotic cells using a novel assay that employs ligation of DNA fragments in situ to selectively label apoptotic cells. The assay may be used in combination with known in situ methodologies to simultaneously detect apoptotic cells and specific biomolecules present in the apoptotic cell.

81 Claims, 4 Drawing Sheets

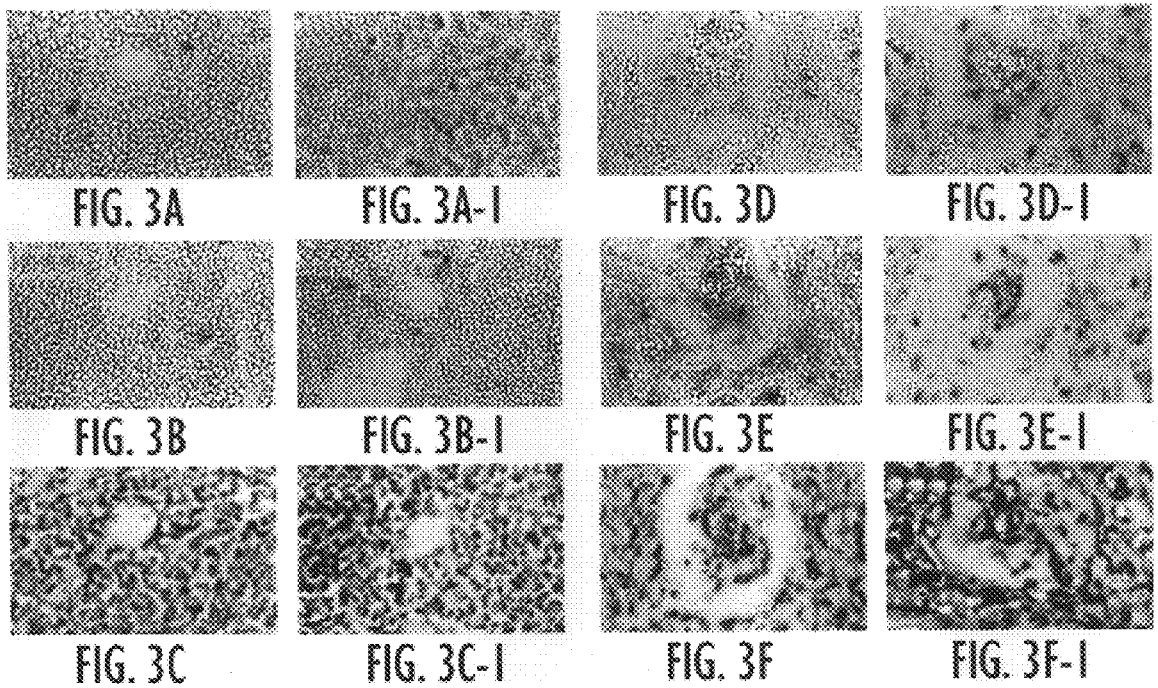
FIG. 3A  FIG. 3A-1  FIG. 3D  FIG. 3D-1
FIG. 3B  FIG. 3B-1  FIG. 3E  FIG. 3E-1
FIG. 3C  FIG. 3C-1  FIG. 3F  FIG. 3F-1
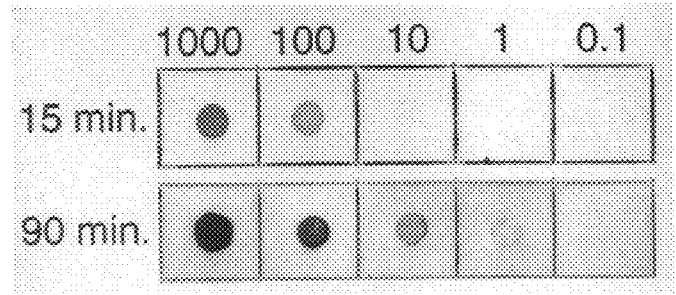
FIG. 4

SEQUENCE LISTING (1) GENERAL INFORMATION:

(iii) NUMBER OF SEQUENCES: 2

(2) INFORMATION FOR SEQ ID NO:1:

-continued

```
    (i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: DNA (vi) ORIGINAL SOURCE:

(vii) IMMEDIATE SOURCE: pBluescript-bSDI1

(xi) SEQUENCE DESCRIPTION: SEQ ID NO:1:

GTGGCCTGCC CAAGCTCTAC CT                                              22

(2) INFORMATION FOR SEQ ID NO:2:

(i) SEQUENCE CHARACTERISTICS:
        (A) LENGTH: 28  base pairs
        (B) TYPE: nucleic acid
        (C) STRANDEDNESS: single
        (D) TOPOLOGY: unknown (ii) MOLECULE TYPE: DNA (vi) ORIGINAL SOURCE:

(xi) SEQUENCE DESCRIPTION: SEQ ID NO:2:

GGCTGGTCTG CCGCCGTTTT CGACCCTG                                        28
```

ASSAY FOR DETECTING APOPTOTIC CELLS

The invention described herein was made with government support, and the government has certain rights in the invention.

FIELD OF THE INVENTION

This invention relates generally to the fields of molecular biology and cell biology and, more specifically, to apoptosis and methods for detecting apoptosis in biological samples.

BACKGROUND OF THE INVENTION

Apoptosis is a process of programmed cell death by which multicellular organisms selectively delete cells. The term necrosis is used to describe the morphological changes undergone by cells that die by processes other than apoptosis. Apoptosis is characterized by a progressive condensation of the chromatin to the inner face of the nuclear membrane, cell shrinkage with consequent loss of membrane contact with neighboring cells, and fragmentation of the cells with formation of membrane-bound acidophilic globules (apoptotic bodies).

The DNA of cells that have undergone apoptosis is cleaved into fragments that are multiples of approximately 180 base pairs. These fragments can be seen after agarose gel electrophoresis as a characteristic "ladder" develops. This ladder is widely used as a biochemical marker for discriminating apoptotic cell death from necrotic cell death as the DNA of necrotic cells is randomly degraded and does not produce a ladder. The ladder develops as a result of cleavage of nuclear DNA within the linker regions between nucleosomes (1,2). Double strand cleavage results from frequent nicks on both DNA strands (3).

Although the endonuclease responsible for the cleavage of DNA in apoptotic cells has not been definitively identified, candidate nucleases with properties consistent with their involvement in apoptosis have been identified in apoptotic cells (4–6).

The endonucleases that have been identified in apoptotic cells are generally similar in their properties to pancreatic DNase I (7). Specifically, these endonucleases share the following characteristics:

(i) the DNA ends produced by DNase I cleavage (5'-phosphate and 3'-hydroxyl) are the same as those found in apoptotic nuclei (8–10);

(ii) DNase I-transfected COS cells show chromatin changes similar to those seen in apoptosis (11); and (iii) DNase I cleavage of chromatin produces the same characteristic nucleosomal DNA fragments that can be isolated from apoptotic cells (1).

Although DNase I has been detected in cells undergoing apoptosis and the tissue distribution of DNase I is consistent with a role in apoptosis (12, 13), the endonucleases partially purified from apoptotic cells were shown to be distinct from DNase I (4–6). There is less evidence for the involvement of DNase II and other endonucleases in apoptosis (14, 15).

Presently, the terminal deoxynucleotidyl transferase (TdT)-mediated biotinylated dUTP nick end labeling (TUNEL) method is used to detect apoptotic cells in tissue sections. The TUNEL method utilizes TdT to incorporate a biotinylated deoxyuridine label into DNA fragments containing a 3'-hydroxyl group. The label can be detected using a variety of avidin/streptavidin based detection methodologies. Although 3'-hydroxyl groups are present in the double stranded DNA breaks in the apoptotic cells, they are also present in the DNA of cells that have undergone necrotic cell death. This method, therefore, is not suitable for distinguishing between necrotic cell death and apoptotic cell death. (40, 41) In addition, this methodology does not permit the simultaneous detection of 3'-hydroxyl groups and other biologically relevant molecules, such as RNA and proteins.

Presently, there is a need in the art for a methodology to specifically detect apoptotic cells. There is presently no methodology that permits the specific detection of apoptotic cell death without the simultaneous detection of necrotic cells. In the experiments reported here, we determined whether DNA double strand breaks characteristic of those produced by an endonuclease like DNase I can be detected in apoptotic cells in situ.

When DNA is bound to histones or other proteins in chromatin, it is partially protected from the action of endonucleases, which are able to cleave the DNA at approximately 10-bp intervals, the distance of a single helical turn of the DNA (16). Because of the helical twist of DNA, the two strands are accessible to endonucleases with production of staggered ends as well as some blunt ends. Thus DNase I cleavage of nucleosome-bound DNA gives rise to double strand cuts with 1, 2, or 3 bases of 3' overhang (17, 18).

In contrast, DNase II cleavage of DNA in chromatin yields longer 3'-overhangs of an average of 4 bases (16, 18).

SUMMARY OF THE INVENTION

To detect double-stranded DNA ends in apoptotic nuclei in situ, we used two kinds of double-stranded labeled DNA fragments which were ligated to DNA ends present in the nuclei of cells in sections of fixed paraffin-embedded tissues. To detect single-base 3'-overhangs, we took advantage of the fact that double-stranded DNA fragments synthesized by Taq DNA polymerase in the polymerase chain reaction have a single 3' base extension beyond the templated sequence. Although it was originally suggested that Taq polymerase added only deoxyadenosine to the 3'-ends of double-stranded DNA (19), other work subsequently established that if the last templated 3'-nucleotide synthesized is deoxycytidine, Taq polymerase will add deoxyadenosine or deoxycytidine, leaving no blunt-ended DNA (20), thus providing a fragment that could potentially ligate to the recessed 5'-base of many of the single-base 3'-overhangs in a random DNA sequence. For comparison, a fragment ligatable only to blunt ends was synthesized by Pfu DNA polymerase, because this polymerase produces blunt-ended products only (20). By this procedure we determined that apoptotic nuclei, but not nuclei in necrotic tissue or tissue with other non-apoptotic DNA damage, have DNA ends ligatable to labeled DNA fragments with single-base 3' overhangs. In contrast, nuclei with all forms of DNA damage have a high concentration of 3'-hydroxyl DNA ends that are a substrate for terminal deoxynucleotidyl transferase (TdT) (21). As TdT can extend the 3' base of single-stranded DNA and overhanging, blunt, and recessed 3' bases of double-stranded DNA (22), TdT based methodologies are not suitable to distinguish apoptotic cells from necrotic cells. In contrast, ligation based methodologies are suitable to accomplish this very desirable objective.

The present invention provides a methodology for specifically detecting the presence of apoptotic cells in tissue sections. The present invention overcomes the limitations of the prior art by employing a novel ligation methodology to detect DNA fragments that are diagnostic of apoptotic cells.

One aspect of the present invention includes a method for detecting apoptotic cells in tissue sections. This method uses a novel in situ ligation methodology to label double strand DNA breaks with overhanging termini diagnostic of apoptotic cells.

Another aspect of the present invention is to provide a method of detecting and isolating DNA fragments that have defined termini using a solid phase capture assay.

Another aspect of the invention includes a method for detecting the presence of apoptotic cells in a tissue sample using the ligation methodology presented herein in a DNA blot format. The DNA is isolated from the sample and fractionated by size using agarose gel electrophoresis. The DNA is then transferred to a solid support and probed using the ligation methodology. This method is more sensitive than currently available technologies and permits the detection of a small number of apoptotic cells when the apoptotic cells form only a small portion of the tissue sample.

Another aspect of the present invention is to provide a method for detecting the presence of biologically important macromolecules in a cell undergoing apoptosis. These macromolecules include proteins and RNA. This method permits the simultaneous detection of an apoptotic cell and the detection of the presence of specific macromolecules within the apoptotic cell.

Another aspect of the present invention is to provide a methodology for analyzing DNA to determine whether the DNA has been acted upon by a nuclease and, if the DNA has been acted upon by a nuclease, to determine what type of nuclease has acted upon the DNA.

Another aspect of the invention is to provide a method that allows the determination of the nature of DNA damage caused by the activity of nucleases upon the DNA and specific RNA synthesis associated with that damage.

BRIEF DESCRIPTION OF THE DRAWINGS

FIGS. 1A–1C'. Detection of different types of DNA ends within apoptotic cells in rat thymus.

FIGS. 3(A)–3(F'). Detection of DNA ends within necrotic cells in Wilms' tumor by three labeling methods.

FIG. 4. Relative color development of spots with various amounts of digoxigenin-labeled DNA.

DETAILED DESCRIPTION OF THE INVENTION

Figure 2A:
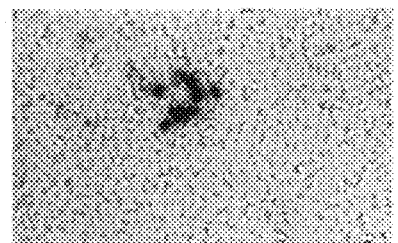
FIGS. 2A–2D. Comparison of patterns of apoptotic cells, detected by the presence of different types of DNA ends, in control and glucocorticoid-treated thymus.
Figure 2A:
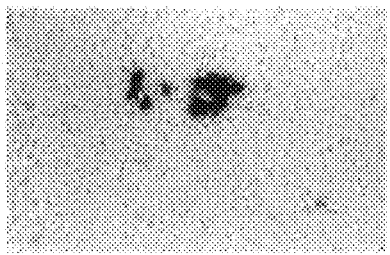
Figure 2A:
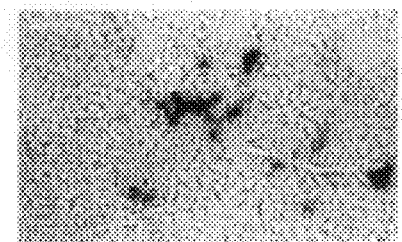
Figure 2A:
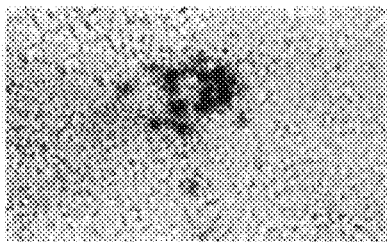
Figure 2A:
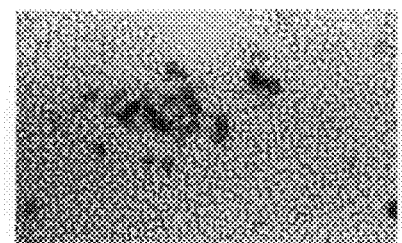
Figure 2A:
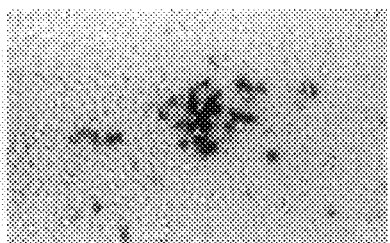
Figure 2A:
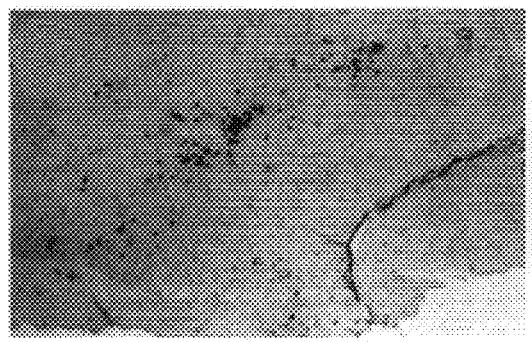
Figure 2C:
Figure 2B:
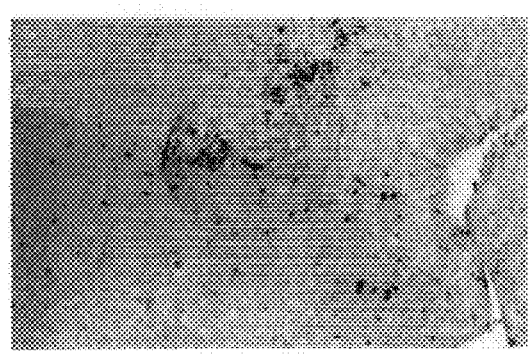
Figure 2D:

The present invention may be more easily understood with reference to the following non-limiting examples.

EXAMPLES

General Methods
Preparation of Double-strand Nucleic Acid Fragments for In Situ Ligation In the following specific examples, the present invention is described in terms of DNA probe molecules. Those skilled in the art will readily appreciate that, for the purposes of the present invention, RNA probe molecules are equivalent to DNA probe molecules and could be substituted into the methods and kits of the present invention by simply employing an RNA ligase enzyme instead of a DNA ligase enzyme. Thus, the phrase "nucleic acid," as used herein and particularly in the claims, includes both RNA and DNA molecules.

A 226-bp double-stranded DNA fragment was prepared using primers 5'-GTGGCCTGCCCAAGCTCTACCT-3' and 5'-GGCTGGTCTGCCGCCGTTTTCGACCCTG-3' complementary to plasmid pBluescript-bSDI1 (23). Although we used this sequence for the data presented here, the actual sequence of the fragment used is unimportant because we used unrelated sequences of lengths 60 to 450 bp with equivalent results. To prepare fragments by the polymerase chain reaction (PCR) with Taq polymerase we set up reactions comprising 100 $\mu$l of 50 mM Tris-Hcl, pH 8.3, 10 mM KCl, 1.5 mM MgCl2, 16.6 $\mu$M digoxigenin-11-dUTP (Boehringer Mannheim), 16.6 $\mu$M TTP, 50 $\mu$M dATP, 50 $\mu$M dCTP, 50 $\mu$M dGTP (other nucleotides from Sigma), 100 pmol of each primer, and 10 pg of plasmid. These concentrations of reagents are appropriate for most applications. In some instances, it may be desirable to increase the incorporation of label into the probe and thereby increase the sensitivity of the assay by omitting TTP from the reaction mixture. Taq polymerase (2.5 units, Boehringer Mannheim) was added to each tube when the reaction mixture had been heated to 80° C. PCR was performed with 35 cycles of 20 seconds at 95° C., 20 seconds at 61° C., and 120 seconds at 74° C., the final cycle having an extension time of 4–10 minutes. Fragments were prepared using cloned Pfu polymerase (Stratagene) using the same protocol but with a buffer composition of 200 mM Tris-HCl pH 8.8, 100 mM KCl, 100 mM ammonium sulfate, 20 mM MgSO4, 1% Triton X-100 and 1 mg/ml BSA. Agarose gel electrophoresis of an aliquot of the reaction showed a single product for both enzymes.

To precipitate the fragments ammonium acetate was added to 2.5 M, the solution was centrifuged at 10,000 g for 5 minutes, and the supernatant was mixed with 2 volumes ethanol and centrifuged for 25 minutes. The supernatant was discarded and the pellet was washed with 70% ethanol and then with 100% ethanol. After vacuum drying for 20 minutes, the pellet was dissolved in water and the concentration measured by Hoechst dye 33258 fluorescence (24). In an alternative protocol, the PCR reaction mixture was subjected to column purification using silica glass columns (High Pure, Boehringer Mannheim). The fragments were stored at −20° C. until use.

In various embodiments the DNA probe molecule may incorporate different detectable moieties. These detectable moieties may be enzymes, small molecules, chromophores, fluorophores or radio-labeled molecules. Small molecules are seen to include biotin, digoxigenin, and single atoms such as bromine. In a preferred embodiment, bromine will be used in the form of bromo deoxyuridine. Radio-labeled molecules is seen to include single atoms, such as radioactive iodine, as well as larger molecules.

Ligation of Labeled DNA Fragments

Digoxigenin-labeled probe fragments were ligated to DNA in tissue sections in situ using T4 DNA ligase. Various tissues (described in Examples) were used with the following protocol. Tissue fragments were fixed in either freshly prepared paraformaldehyde or buffered formaldehyde, with equivalent results, and were conventionally dehydrated and embedded in paraffin. 6-$\mu$m sections were treated with xylene to remove the paraffin and rehydrated in graded alcohol concentrations. The rehydration was accomplished by incubating the sample in xylene for 5 minutes then replacing the xylene with fresh xylene and incubating a second 5 minute interval. The xylene was removed and the sample was incubated in 100% ethanol for 5 minutes. The ethanol was then removed and fresh 100% ethanol was added. The sample was incubated for an additional 5 minutes in 100% ethanol. The ethanol was then replaced with 96% ethanol and the sample was incubated for 30 seconds. The 96% ethanol was then replaced with 80% ethanol and the sample was incubated for 30 seconds. The 80% ethanol was then removed and the sample washed in water.

All the following procedures were performed at room temperature (23° C.). The de-paraffinized sections were incubated with 50 µg/ml proteinase K in PBS for 30 minutes, then rinsed thoroughly with water. A mix of 50 mM Tris-HCl, pH 7.8, 10 mM MgCl2, 10 mM DTT, 1 mM ATP, 25 µg/ml BSA, 15% polyethylene glycol (8000 m.w., Sigma), with the digoxigenin-labeled DNA fragment at 1 µg/ml and DNA T4 ligase (Boehringer Mannheim) at 25–100 units/ml was added (20 µl per section). Sections were covered with glass coverslips and placed in a humidified box for 1–16 hours. The sections were thoroughly washed in water and then pre-blocked with blocking solution (Boehringer Mannheim), reconstituted as recommended by the manufacturer, for 15 minutes. Additional washes with 70° C. water can be used to inactivate endogenous alkaline phosphatases if excessive background staining is observed. The blocking solution was removed and sheep anti-digoxigenin Fab fragment-alkaline phosphatase conjugate (Boehringer Mannheim), 1:100 dilution in blocking buffer, was added for 10 minutes, followed by washing in 0.1 M Tris-HCl, pH 7.5, 0.1 M NaCl, 2 times for 10 minutes each. For color development, sections were then placed in the solution recommended by the manufacturer (0.1 M Tris, pH 9.5; 0.1 M NaCl; 167 µg/ml 5-bromo-4-chloro-3-indolyl phosphate; 330 µg/ml nitro blue tetrazolium) and the color development was monitored under the microscope. The reaction was stopped by washing sections in water. The wet sections were photographed without counterstain.

The ligation reaction may also be performed on isolated DNA that has been size fractionated on an agarose gel. The DNA is first transferred to a solid support by any conventional means, i.e. capillary action, vacuum blotting or electroblotting. The solid support is then blocked and the ligation reaction conducted as above.

Terminal Deoxynucleotidyl Transferase (TdT) Reaction

For the reaction of available DNA 3'-hydroxyls with TdT, the published procedure was used (21) modified to accommodate the use of digoxigenin as label rather than biotin. Instead of addition of ligase mixture as above, a mixture comprising 30 mM Tris-HCl, pH 7.2, 140 mM sodium cacodylate, 1 mM cobalt chloride, 0.1 mM DTT, 50 µm digoxigenin-dUTP and 300 units/ml TdT (Promega) (20 µl per section) was added for 1 hour at 37° C. in a humidified incubator. The washing and visualization of incorporated digoxigenin was as described above.

Tissues

Thymus: To prepare tissue that contained a large number of apoptotic cells, Sprague-Dawley rats (150 g) were injected subcutaneously with 6 mg/kg dexamethasone (Sigma) dissolved in 30% dimethyl sulfoxide in water. Animals were killed after 24 hours and the thymus was fixed in 4% paraformaldehyde. Thymus from control animals was obtained and fixed in the same way. After 18 hours in paraformaldehyde the tissue fragments were placed in 70% ethanol and taken through graded alcohols to 100% ethanol, placed overnight in chloroform, and then embedded in paraffin.

Necrotic tissue: Sections from a Wilms' tumor from a 5-year old male patient, containing extensive areas of necrosis, as often encountered in such tumors (25), was used as to provide sections with large numbers of necrotic cells.

Hydrogen peroxide treated liver: Random DNA damage was induced by injection of hydrogen peroxide. Sprague-Dawley rats were anesthetized and 100 µl of 30% hydrogen peroxide was injected superficially in the liver in several locations. After 20 seconds the liver was excised from the animal and the hydrogen-peroxide-treated segment of the liver was fixed in 4% paraformaldehyde, with multiple changes of the solution to remove any remaining hydrogen peroxide. Segments of tissue from a distal region of the liver were fixed as controls. The tissues were then processed as described for thymus.

Tissue for in vitro autolysis: 5-mm fragments of bovine adrenal gland were placed in culture medium in a 37° C. incubator for 16 hours (26). They were then fixed and processed as described for thymus.

Heated tissue sections: Sections from a control bovine adrenal gland were de-paraffinized, rehydrated through graded alcohol concentrations, placed in 0.01 M sodium citrate, pH 6.0, and heated at 100° C. for 5 minutes.

Spotting of Digoxigenin-labeled DNA on Nylon

Different amounts of digoxigenin-labeled DNA (synthesized byrandom-primer method, Boehringer Mannheim) were spotted on Hybond-N membranes (Amersham) as previously described (27). The digoxigenin fixed to the membranes was detected using the same protocol as described above for tissue sections, except that anti-digoxigenin-alkaline phosphatase conjugate was used at 1:5000 dilution.

Preparation of Probe Fragments with Varying Overhangs

PCR is performed on a DNA template that includes a DNA sequence that functions as the recognition site for a restriction enzyme. The PCR product is purified and isolated by standard means. The PCR is performed in the presence of a small amount of dideoxynucleotides. This results in fragments that terminate in a dideoxynucleotide. These fragments do not contain a 3'-hydroxyl group and cannot be ligated into target DNA.

The PCR product is then digested with a restriction enzyme that recognizes the included site. Cleavage with a restriction endonuclease generates 3'-OH at the cleavage site. Fragments thus cleaved can be ligated into target DNA. The characteristics of the termini of the digested fragment will be determined by the restriction enzyme chosen. By incorporating two identical appropriately spaced recognition sites into the DNA template, fragments having defined termini can be produced. Alternatively, two oligonucleotides having complementary regions and overhanging regions can be synthesized. The oligonucleotides can be annealed by standard techniques. Information concerning restriction enzyme recognition sites, appropriate digestion conditions and the characteristics of the resulting termini are readily available to one skilled in the art by consulting a standard text such as Sambrook et al., Molecular Cloning: A Laboratory Manual 2nd Edition, Cold Spring Harbor Press, specifically incorporated herein by reference.

Analyzing DNA to Determine the Types of Termini Present

The termini produced by various nuclease enzymes have previously been determined. By determining the types of termini present in a DNA sample, it is possible to gain information about the nuclease enzymes that have acted upon the DNA. To determine if the DNA in a given sample has been acted upon by a nuclease, the DNA is probed with various nucleic acid fragments. Each nucleic acid fragment used as a probe will have termini capable of ligating to the termini produced by a specific type of nuclease. By determining which fragment can be ligated to the DNA sample, it is possible to determine what nuclease has acted upon the sample. This process may be conducted by dividing the sample into aliquots and probing each aliquot with a different fragment. Alternatively, multiple fragments may be tested simultaneously on the same sample. In this case, the fragments may be distinguished from each other by the incorporation of different detectable moieties. The detectable moieties may be enzymes, small molecules, chromophores, fluorophores, or radio-labeled materials. Those skilled in the art can readily select suitable detectable moieties so as to permit the simultaneous detection of each moiety.

In a preferred embodiment, a number of double stranded nucleic acid probe molecules, either DNA or RNA or a mixture of both, can be fixed to different regions of a solid support. A DNA sample suspected of containing termini generated by the action of one or more nucleases, may be brought into contact with the fixed nucleic acid probe molecules in the presence of appropriate ligase enzymes and co-factors (metal ions, ATP, buffers, etc.).

The DNA sample is incubated with the nucleic acid probe molecule at an appropriate temperature of from about 10° C. to about 37° C. for an appropriate length of time of about 30 minutes to about 16 hours. After incubation, the solid support may be washed to remove any unligated DNA and the presence of DNA ligated to the probe molecules is detected.

In an alternative embodiment, an aliquot of the DNA suspected of containing termini created by the action of one or more nuclease enzymes may be fixed to a solid support using any art recognized means, such as, for example, UV treatment. The fixed DNA can then be contacted with a solution containing one or more nucleic acid probe molecules, DNA, RNA, or a mixture of both, and the appropriate ligase enzymes. The probe molecules will be selected to contain detectable moieties. The detectable moieties will be selected so that each moiety will be detectable in the presence of the detectable moieties present on the other nucleic acid probe molecules and, ideally, all moieties will be simultaneously detectable.

After a suitable period of time to permit the ligation of the probe molecules to the DNA termini present in the aliquot, the solid support may be washed and the presence of nucleic acid probe molecules detected.

The detection of nucleic acid probe molecules will be performed using art recognized methods. For example, the nucleic acid probe molecule may incorporate a detectable moiety that can be directly detected. In this embodiment, the detectable moiety may be a chromophore, fluorophore, or enzyme.

In an alternative embodiment, the nucleic acid probe molecules will include detectable moieties that can be bound by a reagent comprising a molecule having a binding portion and a signaling portion. Examples of suitable binding portions include, but are not limited to, avidin, streptavidin, antibodies, and antibody fragments. Preferred embodiments include a detectable moiety that is a bromine atom incorporated into a nucleic acid probe molecule and a binding portion that comprises an anti-bromine antibody. Other preferred embodiments include detectable moieties that are biotin or biotin analogs and binding portions that comprise avidin or streptavidin. Other preferred embodiments utilize digoxygenin as a detectable moiety and a binding portion that comprises an antidigoxygenin antibody or antibody fragment.

In embodiments that utilize a reagent that comprises a molecule that binds to a detectable moiety, the molecule may also comprise a signaling portion that permits detection of the presence of the reagent. For example, the reagent may comprise a molecule having a binding portion that binds to the detectable moiety, and the molecule may additionally comprise a signaling portion that permits detection of the molecule. Examples of signaling portions include enzymes, chromophores, fluorophores, and radio labeled material. Thus, the molecule may comprise a binding portion covalently attached to a signaling portion. Examples include, but are not limited to, avidin or streptavidin covalently attached to enzymes, such as luciferases, peroxidases, galactosidases, glucuronidases, and phosphatases. Preferred embodiments will use streptavidin covalently attached to horseradish peroxidase. Other preferred examples include antibodies coupled directly with enzymes. Those skilled in the art are aware that such coupling may be accomplished using a variety of coupling reagents such as those sold by Pierce Chemical Co. of Rockford, Ill. Examples include anti-bromine antibody coupled to enzymes. Preferred examples include anti-bromine antibody attached to horseradish peroxidase.

In some embodiments of the instant invention, detection of the detectable moiety is accomplished by contacting the detectable moiety with a reagent that comprises a first molecule that binds to the detectable moiety and then subsequently applying a reagent that comprises a second molecule that binds to the first molecule. For example, when the detectable molecule is bromine, the sample may be contacted with a reagent that comprises an anti-bromine antibody or antibody fragment. The sample may then be contacted with a reagent that comprises a second molecule that binds to the anti-bromine antibody or antibody fragment. Examples include, but are not limited to, reagents comprising protein A, lectins, and antibodies that bind to the anti-bromine antibody coupled to a signaling portion. The second molecule may contain a signaling portion. The signaling portion may include an enzyme, chromophore, fluorophore, or radio-labeled material. The preparation and utilization of such second molecules are well known to those skilled in the art. (See, for example, chapter 18 of Sambrook, et al. (42)) Other examples include the use of biotin or biotin analogs as detectable moieties, streptavidin or avidin as first molecules, and anti-streptavidin or anti-avidin antibody or antibody fragments coupled to signaling portions as second molecules. Other preferred embodiments utilize digoxygenin as detectable moieties, anti-digoxygenin antibodies as first molecules, and antibodies directed against the anti-digoxygenin antibodies coupled to signaling portions as second molecules.

In embodiments that utilize a first binding molecule to bind a detectable moiety and a second molecule to bind the first molecule, the second molecule may contain a signaling portion. The signaling portion may be any signaling portion known in the art. Signaling portions of the present invention include, but are not limited to, chromophore, fluorophores, enzymes, and radio-labeled material. When the signaling portion is a chromophore or fluorophore, the presence of the signaling portion may be detected visually or with the use of devices that measure optical density. When utilizing optical density readers, it may be desirable to place the sample on or in a solid support that is transparent at the wavelength at which the chromophore absorbs or at the wavelengths at which excitation and emission of the fluorophore occur. This methodology may be useful to quantify the presence of termini generated by specific nucleases. Transparent solid supports are seen to include, but are not limited to, transparent test strips and microtiter plates.

When the signaling portion is an enzyme, the method will include a step of providing the enzyme with a substrate. The substrate may be provided as part of the reagent comprising the second molecule. Alternatively, the substrate may be provided after the reagent comprising the second molecule. When the enzyme reacts with the substrate, some measurable change must take place. For example, the enzyme may convert a colorless substrate molecule into a colored product molecule. Alternatively, a colored substrate molecule may be converted into a colorless product molecule. In some instances, one of the products of the enzyme reaction may be a photon of light. In these instances, the quantity of photons of light produced can be measured. The available enzymes and appropriate substrates and quantitative methodologies are well known to those skilled in the art.

Example 1
Detection of High Concentrations of Double-stranded DNA with Single-base 3'-overhangs as well as Blunt-ended DNA and Free 3'-ends, in Apoptotic Cells.

Figure 6A:
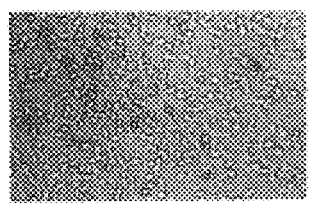
FIGS. 6A–6C'. Detection of DNA ends within autolytic bovine adrenocortical tissue.
Figures 1, 6A:
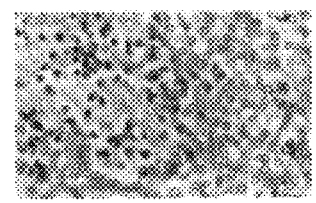
Figure 6B:
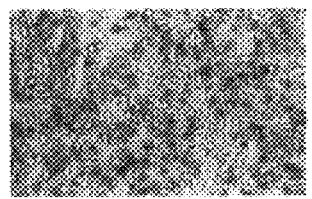
Figures 1, 6B:
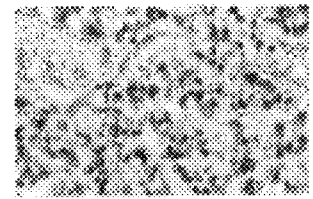
Figure 6C:
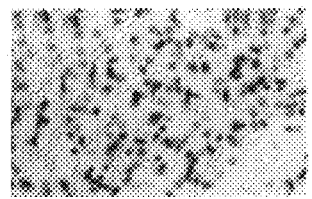
Figures 1, 6C:
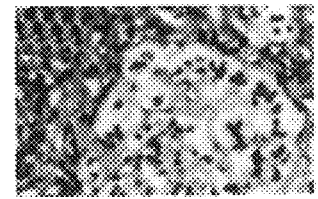
Figure 8:
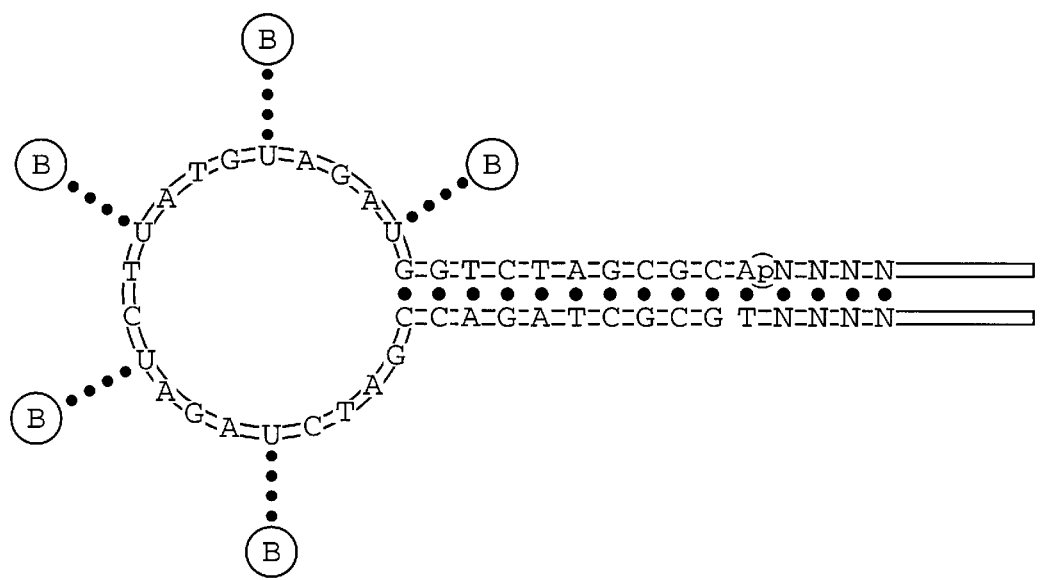

Rat thymus was fixed and processed by three labeling methods as described in the General Methods. FIG. 1 shows the reaction products resulting from (a) ligation of single-base 3' overhang double-stranded DNA fragment prepared by Taq polymerase, using 15 minutes of alkaline phosphatase color development; (b) ligation of blunt-ended DNA fragment prepared by Pfu polymerase, using 15 minutes of alkaline phosphatase color development; (c) extension of 3' hydroxyls with TdT, using 7 minutes of alkaline phosphatase color development. FIGS. 1A-1, 1B-1, and 1C-1 show the reaction products of the 3 labeling methods using 6-fold longer times of alkaline phosphatase color development (90 and 42 minutes respectively).

To obtain a tissue with many apoptotic cells we initially used rat thymus 24 hours after administration of glucocorticoid, a model for apoptosis well established by previous investigators (1). However, control rat thymus also had a lower but useful number of apoptotic cells, consistent with the observation that about 1% of thymic cells show features of cell death in postnatal animals (28). Because control thymus tissue sections were not affected by the severe atrophy found in glucocorticoid-treated thymus, we used the apoptotic cells in control thymus as our standard for the investigation of DNA ends, but we show also for comparison the results in thymus from dexamethasone-treated animals.

Consecutive 6 μm sections were labeled with single-base 3' overhang and blunt-ended DNA fragments, using the same concentration of fragment and the same period of time of incubation with ligase. Consecutive sections were also labeled with TdT. In all cases the digoxigenin fixed to the section by the action of ligase or TdT was detected using an anti-digoxigenin-alkaline phosphatase conjugate. We assessed the length of time of the color development in the alkaline phosphatase reaction which just allowed the visualization of apoptotic cells. A reaction time of 7 minutes in the case of TdT and 15 minutes for ligase (using either 3'-overhang or blunt-ended DNA fragments) was sufficient to label apoptotic cells in thymus sections. When 6-fold longer times of color development were used, the same number of nuclei were labeled, using all three techniques, with very little background staining.

Example 2
Comparison of Patterns of Apoptotic Cells, Detected by the Presence of Different Types of DNA Ends, in Control and Glucocorticoid-treated Thymus.

Thymus from control (a, b) and glucocorticoid-treated (c, d) rats were fixed and processed as described in Example 1. FIG. 2 shows the reaction products resulting from (a, c) ligation of Taq polymerase fragment, 15 minutes of alkaline phosphatase reaction; (b, d) TdT reaction, 7 minutes of alkaline phosphatase reaction.

We compared the labeling of cells by ligation of 3'-overhang fragments labeling of accessible 3' ends, in both control and glucocorticoid-treated thymus (FIG. 2). The numbers and patterns of cells stained by both methods in thymic cortex in control and glucocorticoid-treated animals were consistent with the previously reported numbers and patterns of apoptotic cells in control animals and in animals 24 hours after glucocorticoid administration (28–30).

Example 3
Detection of DNA Ends within Necrotic Cells in Wilms' Tumor by Three Labeling Methods.

The methods used were as described in Example 1. Serial sections were used and the same regions are shown by the three labeling methods. (a, d) ligation of Taq polymerase fragment, 15 minutes of alkaline phosphatase reaction; (b, e) ligation of Pfu polymerase fragment, 15 minutes of alkaline phosphatase reaction; (c, f) TdT reaction, 7 minutes of alkaline phosphatase reaction. FIGS. 3A-1, 3B-1, 3C-1, 3D-1, 3E-1, and 3F-1 show the reaction products of the 3 labeling methods using 6-fold longer times of reaction with alkaline phosphatase (90 and 42 minutes respectively).

To compare the occurrence of single-base 3' overhangs, blunt ends, and all accessible 3' ends in apoptotic and necrotic cells, we performed simultaneous staining of both apoptotic and necrotic tissue. Sections of Wilms' tumor, containing large areas of necrosis, were used as a standard for a tissue comprising many necrotic cells. Consecutive sections were used to enable comparison of the reaction of different methods on various areas within this heterogeneous tissue. Staining reactions were performed for two different times, as used in the detection of apoptotic cells in thymus: a time sufficient for visualization of apoptotic cells (7 or 15 minutes) and a time 6-fold longer. To ensure that these times were appropriate, sections of rat thymus were mounted on the slide together with the necrotic tissue and processed in the same labeling solutions. In necrotic areas of the specimen, the TdT reaction produced intense labeling even with 7 minutes of alkaline phosphatase color development (FIG. 3). In purely necrotic regions (FIGS. 3, a–c), ligation of both 3'-overhang and blunt-ended fragments produced very little staining even with 6-fold longer color development than required for visualization of apoptotic cells. In adjacent areas of the tumor, where some tissue structure was preserved (FIGS. 3, d–f), extensive staining of nuclei with TdT was again observed. Distinct labeling of nuclei was also observed with 6-fold overdevelopment of the color reaction in the case of blunt-ended fragment, but hardly at all with the 3'-overhang fragment. This leads to the conclusion that single-base 3' overhangs are specific for apoptotic cells.

Example 4
Relative Color Development of Spots with Various Amounts of Digoxigenin-labeled DNA.

The indicated amounts of digoxigenin-labeled DNA were spotted onto nylon membranes as described in Methods and then processed for detection of digoxigenin by the alkaline phosphatase reaction. The extent of color development at 15 and 90 minutes is shown.

To provide an estimate of the relative abundance of single-base 3'-overhangs in apoptotic versus necrotic tissue, a series of spots of digoxigenin-labeled DNA on nylon was stained by alkaline phosphatase color development using the same two times used for tissue sections (FIG. 4). This experiment shows that 90 minutes versus 15 minutes of color development allows the visualization of almost 100-fold less digoxigenin. Since apoptotic nuclei in thymus are readily detectable by ligation of 3'-overhang fragment using 15 minutes of color development, but nuclei in necrotic tissue are hardly stained with 90 minutes of color development, it may be concluded that apoptotic nuclei have at least 100-fold more single-base 3' overhangs than necrotic nuclei.

Example 5
Testing of the 3'-overhangs in Cells with DNA Damage

In order to assess the specificity of the present methodology, we tested whether DNA ends ligatable to 3'-overhang DNA fragment were present in cells with other types of DNA damage that might be produced in vivo (e.g., oxygen free radical DNA strand breakage), or by postmortem autolysis, or by in vitro procedures that damage DNA (e.g. heating, as used in antigen retrieval procedures). In order to assess this, detection of DNA ends within hydrogen peroxide-treated liver by two labeling methods.

Figure 5A:
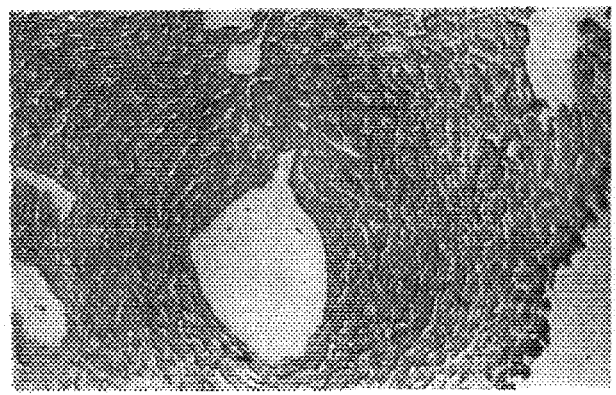
FIGS. 5A–5B. Detection of DNA ends within hydrogen peroxide-treated liver by two labeling methods.
Figure 5B:
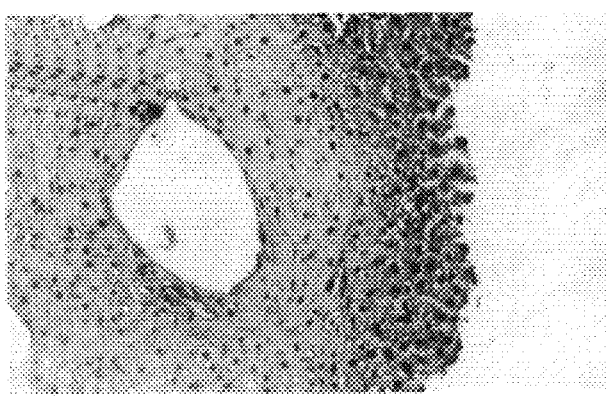

The methods used were as described in Example 1. FIG. 5 shows serial sections using (a) ligation of Taq polymerase fragment, 90 minutes of alkaline phosphatase reaction; (b) TdT reaction, 42 minutes of alkaline phosphatase reaction.

To provide rapid damage by oxygen radicals, at such a short time that apoptotic cell death was unlikely, hydrogen peroxide was injected into the liver of an anesthetized rat, and segments of liver were fixed 20 seconds later. This tissue showed many areas of nuclei with 3' ends accessible to TdT but no 3' overhangs (FIG. 5).

Example 6
Detection of DNA Ends within Autolytic Bovine Adrenocortical Tissue.

The methods used were as described in General Methods. Serial sections were used and the same regions are shown by the three labeling methods. FIG. 6 shows (a) ligation of Taq polymerase fragment, 15 minutes of alkaline phosphatase reaction; (b) ligation of Pfu polymerase fragment, 15 minutes of alkaline phosphatase reaction; (c) TdT reaction, 7 minutes of alkaline phosphatase reaction. FIGS. 6A-1, 6B-1, and 6C-1 show the reaction products of the 3 labeling methods using 6-fold longer times of reaction with alkaline phosphatase (90 and 42 minutes respectively).

Autolysis was produced within the centers of fragments of bovine adrenal cortex incubated in medium at 37° C. for 16 hours (26). Again using times of alkaline phosphatase color development suitable for the detection of apoptotic cells within rat thymus, no cells were stained by ligation of 3'-overhang fragments, cells were lightly stained with blunt-end fragment ligation, and markedly stained by TdT extension of 3' ends (FIGS. 6, a–c). With 6-fold overdevelopment of the color reaction, light staining was apparent in the sections with 3'-overhang ligation whereas staining with blunt-end fragment and TdT became more intense (FIGS. 6, d–f).

Example 7
Detection of DNA Ends within Heated Tissue Sections by Two Labeling Methods.

Figure 7A:
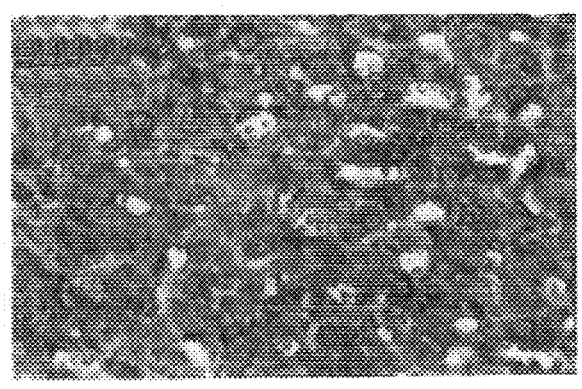
FIGS. 7A–7B. Detection of DNA ends within heated tissue sections by two labeling methods.
Figure 7B:
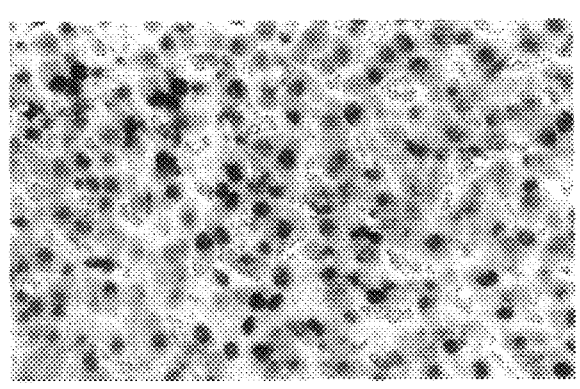

Sections of bovine adrenal gland were treated as described in Methods. FIG. 7 shows serial sections using (a) ligation of Taq polymerase fragment, 15 minutes of alkaline phosphatase reaction; (b) TdT reaction, 7 minutes of alkaline phosphatase reaction.

To test the effects of heat, 6-µm sections of control bovine adrenal gland were heated at 100° C. for 5 minutes followed by ligation of 3'-overhang fragment or detection of accessible 3' ends (FIG. 7). Some nonspecific staining was noted in sections with ligation of 3'-overhang fragment but nuclei were not stained. In contrast, TdT labeling of nuclei was extensive in heated sections.

Example 8
Detection of the Presence of Apoptotic Cells in a Tissue Sample.

DNA present in a sample is isolated according to standard methodologies (see Sambrook, et al.(41). The DNA is size fractionated on agarose and then transferred to a solid support. The solid support is generally in the form of a membrane. The membrane may be constructed of any commonly utilized materials, such as nylon, PVDF or nitrocellulose. The transfer may be accomplished by any commonly utilized methodologies. These methodologies are considered to include capillary action, vacuum blotting and electroblotting.

After the DNA has been transferred to the solid support, the solid support is blocked using known blocking solutions. Subsequent to blocking, the solid support is contacted with the solution containing a DNA probe molecule specific for a target DNA, a DNA ligase enzyme, and the requisite co-factors. The ligation reaction may be conducted at a temperature from about 4° C. to about 37° C. Preferably, the ligation reaction may be conducted at a temperature from about 10° C. to about 37° C. and most preferably at a temperature from about 15° C. to 37° C. One skilled in the art will readily recognize that it is necessary to prevent the solid support from drying out during the process of the ligation reaction. In order to accomplish this, the ligation reaction may be conducted in a sealed container, such as, for example, a sealed plastic bag or a roller bottle or any commonly used device known to those skilled in the art. After completion of the ligation reaction, the solid support is washed and the DNA probe molecule is detected as described above.

Example 9
Simultaneous Detection of 3' Overhangs and Proteins in the Same Apoptotic Cell.

The instant invention permits the simultaneous detection of:

1) DNA molecules characteristic of apoptotic cells; and
2) the protein molecules that are expressed in the same apoptotic cell.

This will allow the characterization of the protein expression of cells undergoing apoptosis. Tissue samples are fixed and embedded in paraffin as described above. The samples are then de-paraffinized and rehydrated through graded alcohol concentrations as described above. The proteinase K step described in the basic protocol is omitted. Instead, the sample is placed in buffer and heated. The samples may be heated by placing them in a sealed container and placing the sealed container in boiling water or, alternatively, may be heated by placing them in buffer and heating the buffer solution in a microwave oven. The samples are heated to a temperature greater than 70° C. and maintained at that temperature for at least 15 minutes. The buffer used may be any commonly available buffer. In a preferred embodiment, the buffer is 0.01 M citrate at a pH of 6.0.

After heating, the samples are cooled and contacted with a solutions containing a DNA probe, a DNA ligase enzyme, the co-factors necessary for the ligase reaction to proceed, and an antibody specific to a protein of interest. The antibody is detected using standard methods and the DNA probe molecule is detected as described above. The presence of the antibody and the DNA molecule in the same cell indicates that the protein for which the antibody is specific is present in apoptotic cells.

In a preferred embodiment, after heating, a first antibody may be applied to the sample and incubated for an appropriate period of time, such as from about 5 minutes to about 48 hours, at an appropriate temperature, such as from about 4° C. to about 37° C. The selection of appropriate times and temperatures is dependent upon the characteristics of the antibody-protein interaction and is well within the skill of the ordinary practitioner in the art.

The sample is then washed with 0.1 M Tris-NaCl at a pH of 7.5 two times for 10 minutes each. The sample is then contacted with a solution containing a secondary antibody conjugated to a detectable moiety. In various embodiments, the detectable moiety may be an enzyme, a small molecule, a fluorophore, a chromophore or a radio-labeled molecule. In a preferred embodiment, the enzyme will be an alkaline phosphatase.

The sample is incubated with the secondary antibody for an appropriate period of time, such as from about 5 minutes to about 24 hours, at an appropriate temperature such as from 4° C. to 37° C. In a preferred embodiment, the secondary antibody is incubated with the sample at room temperature for 30 minutes. The sample is then washed in a buffer solution, such as Tris-NaCl at pH 7.5. When the detectable moiety is an enzyme, the sample is contacted with a solution containing a detection reagent. The detection reagent may commonly be a molecule that serves as a substrate for the enzyme conjugated to the secondary antibody. The reaction product of the enzyme and the detection reagent may be detectable. When the enzyme is alkaline phosphatase or horseradish peroxidase, the reaction product may be a chromophore. When the enzyme is a luciferase the reaction product may be photons of light. Other enzymes, known to those skilled in the art, may be used as detectable moieties. Such enzymes are known to those skilled in the art and may be substituted without deviating from the spirit of the invention. Alternative embodiments wherein the detectable moiety is directly attached to the first antibody are within the scope of the invention.

After detecting the presence of the first antibody, the ligase reaction and the detection of a DNA probe molecule are performed as described above may be labeled with a fluorescent dye, and the antibody molecule may be labeled with a different fluorescent dye. The dyes may be selected so that they permit simultaneous detection. The solution containing the DNA probe and the antibody molecule may optionally include blocking agents. Blocking agents used as blocking agents include BSA, dry milk, detergents, and the like. After completion of the reaction, the tissue sample is washed with a buffered solution and examined under a fluorescent microscope. More than one protein molecule can be simultaneously detected. This is accomplished by using antibodies specific for each protein of interest and is limited only by the number of fluorescent dyes that can be simultaneously visualized.

Example 10
Simultaneous Detection of 3' Overhangs and RNA Molecules.

The present invention permits the detection of RNA molecules in cells undergoing apoptosis. Tissue samples are prepared for ligation as described above. The sample is hybridized with an oligonucleotide complementary to the sequence of an RNA molecule of interest. The exact conditions are hybridization are dependent upon the sequence of interest and the length of the oligonucleotide probe. Appropriate methodology for selection of hybridization conditions is contained in Sambrook, et al. Hybridization may be conducted at a temperature from about room temperature to about 74° C. for a period of time from about 15 minutes to 48 hours. Preferably, hybridization may be conducted for a period of time from about 4 hours to about 16 hours, at a temperature from about 40° C. to about 65° C. After hybridization, the sample may be washed. The stringency of the wash conditions, i.e., ionic strength and temperature, are adjusted according to the length of the probe and nucleotide sequence of the probe. After an appropriate period of washing, the sample is contacted with a solution containing a DNA molecule capable of being ligated to a 3'-overhang, a DNA ligase enzyme, and the appropriate co-factors. Ligation reaction is conducted at room temperature for about 1 hour. The sample is then washed and the presence of the oligonucleotide and the DNA molecule are detected. The presence of the oligonucleotide and the DNA molecule in the same cell indicate that the RNA molecule of interest is present in apoptotic cells.

The above assay may be configured in a variety of ways. The oligonucleotide used may be an RNA molecule or a DNA molecule. Detectable moieties may be incorporated into the oligonucleotide. These moieties may be enzymes, small molecules, chromophores, fluorophores or radio-labeled molecules. In a preferred embodiment, the detectable moiety is FITC. Other fluorophores known to those skilled in the art are within the scope of the invention.

Detectable moieties may be incorporated into the DNA molecule to be ligated. For example, the detectable molecules may be enzymes, small molecules, fluorophores, chromophores and radio-labeled molecules. In a preferred embodiment, both the oligonucleotide and the DNA molecule to be ligated incorporate fluorophores. In this embodiment, the fluorophore incorporated in the oligonucleotide fluoresces at a wavelength different from that at which the fluorophore incorporated into the DNA fluoresces. This permits the simultaneous detection of the oligonucleotide and DNA molecule. The DNA molecule that is ligated to the 3'-overhangs in the DNA of the apoptotic cell may contain a small molecule such as biotin, bromine or digoxigenin. After ligation, the sample is contacted with a molecule which binds to the small molecule, such as an avidin or streptavidin when the small molecule is biotin, or anti-digoxigenin antibody or antibody fragment. The molecule that binds to the small molecule is conjugated to a detectable moiety. The detectable moiety may be an enzyme, fluorophore, chromophore or radio-labeled molecule.

Example 11
Solid Support Capture Assay.

The present invention may be used to detect and/or isolate DNA target molecules having deemed overhanging termini. This is accomplished by attaching a nucleic acid probe molecule having a defined terminus to a solid support. The solid support may be any solid support known in the art including, but not limited to, membranes, microtiter plates, agarose beads, beads made of a synthetic resin, and any other solid support known in the art. In a preferred embodiment, the solid support will be a paramagnetic particle coated with a synthetic resin. This embodiment allows facile separation of the beads from the reaction solution.

The nucleic acid probe molecule attached to the solid support is called the capturing fragment. The capturing fragment is selected so as to have a complementary terminus to the defined overhanging terminus of the DNA target molecule. The fragment may be prepared by any means known in the art. For example, the fragment may be prepared from a larger DNA molecule by treatment of the larger molecule with a nuclease that generates the desired overhanging termini. The DNA fragments possessing the desired overhanging termini may then be isolated and subsequently fixed to the solid support, using any methodology known in the art. For example, the solid support may be provided with a reactive functionality that is capable of reacting with functional groups present in the capturing fragment. Alternatively, the capturing fragment may be modified so as to contain a reactive functionality capable of reacting with the solid support. In other embodiments, the capturing fragment will be provided with a small molecule that can be bound by a group present on the solid support. For example, the capturing fragment may be provided with a biotin moiety or a digoxygenin and the solid support with streptavidin or an anti-digoxygenin antibody. Those skilled in the art will readily appreciate that any methodology that does not affect the overhanging terminus of the capture fragment may be used to fix the capture fragment to the solid support.

The capture fragment may be designed so as to contain additional desirable structural characteristics beyond an overhanging terminus. For example, the capturing fragment may be equipped with a restriction enzyme site. After the capturing fragment has been used to isolate the corresponding nuclease-cleaved DNA, the capturing fragment may be cleaved using a restriction endonuclease, thereby liberating a DNA molecule that includes a portion of the capturing fragment in addition to the nuclease cleaved fragment.

The DNA target molecule can be cloned and sequenced using methodologies well known to those skilled in the art. For example, the nuclease-cleaved DNA can be ligated to the capturing fragment. Subsequently, the solid support may be treated with Pfu polymerase to generate blunt ended fragments attached to the solid support. The solid support may then be treated with a restriction enzyme to cleave the blunt ended fragment from the solid support. The fragment can then be cloned into a vector treated so as to have a blunt end and an end that corresponds to the end generated by the restriction enzyme. Those skilled in the art can readily envision other, equivalent cloning strategies. Alternatively, the capturing fragment may be equipped with a sequence to which a PCR primer will bind. After reaction with the nuclease cleaved DNA, the reaction mixture may be provided with the necessary reagents to perform PCR on the captured nuclease cleaved fragment. It is readily apparent to those skilled in the art that more than one desirable functional characteristics can be incorporated into the capturing fragment. For example, both restriction enzyme cleavage sites and PCR primer binding sites may be incorporated into the same capturing fragment.

The capturing fragment may be provided with a detectable moiety. After ligating the nuclease cleaved DNA to the capturing fragment, the capturing fragment may be cleaved from the solid support and the presence of the detectable moiety assayed. It may be necessary to perform a step of isolating capture fragment bound to nuclease cleaved DNA from capture fragment not so bound. Those skilled in the art can readily accomplish this using known methods based upon the difference in size of the two types of fragment.

The DNA suspected of containing nuclease-cleaved ends may be isolated from any source. The DNA is isolated using methodologies readily known by those skilled in the art. After the DNA suspected of containing nuclease cleaved ends is isolated; it is combined with capturing fragment in the presence of DNA ligase and the requisite co-factors, such as divalent metal ions and ATP. After a suitable length incubation, the ligating solution is removed by washing and the presence or absence of nuclease-cleaved DNA can be detected. The basic assay described above can be configured in a variety of ways. For example, the capturing fragment may be provided to the ligation solution as a fragment free in solution. In embodiments of this nature, the capturing fragment will be provided with a binding moiety, such as biotin or digoxygenin. After a suitable reaction period, a solid support containing a molecule capable of attaching to the binding moiety, such as avidin, streptavidin, or anti-digoxygenin, is mixed with the solution. After an incubation period to allow the binding moiety to be attached to the solid support, the solid support can be washed so as to remove unbound material and then treated in any fashion desirable.

Alternatively, the capturing fragment may be provided to the ligation mixture already attached to a solid support. After the ligation reaction is allowed to proceed, the solid support can then be washed as before.

The present invention may be used as an assay to detect termini of a specific overhang present in a DNA sample. After the ligation and attachment to solid support as described above, the sample is washed and then provided with a known quantity of complementary termini. The fragments containing these complementary termini will be detectable in some fashion, for example, as radio labeled or fluorophore or chromophore containing. A second ligation reaction may be performed so as to attach the radio labeled fragments to any remaining overhanging termini that have not bound nuclease treated DNA from the ligation reaction. The more radio labeled material that binds, the fewer correct overhanging termini were present in the original sample.

This invention has been described in terms of specific embodiments set forth in detail, but it should be understood that these are by way of illustration only and that the invention is not limited to the specifically recited embodiments. Modifications and alterations will be readily apparent to those skilled in the art and these modifications and alterations are within the scope of the invention. Accordingly, these modifications and alterations the disclosed invention are considered to be within the scope of the invention and the following claims.

What is claimed is:

1. A method for detecting apoptotic cells in a tissue sample, comprising the steps of:
   fixing a tissue sample;
   contacting the tissue sample with a solution containing a nucleic acid molecule and a nucleic acid ligase enzyme, the nucleic acid molecule being ligatable to a 3'-overhang; and
   detecting the nucleic acid molecule, wherein the detection of the nucleic acid molecule correlates to the presence of apoptotic cells.

2. A method according to claim 1, wherein the nucleic acid molecule comprises a detectable moiety.

3. A method according to claim 2, wherein the detectable moiety is selected from the group consisting of, enzymes, small molecules, chromophores, fluorophores and radio-labeled materials.

4. A method according to claim 3, wherein the detectable moiety is a small molecule selected from the group consisting of digoxigenin, biotin, and bromine.

5. A method according to claim 4, wherein the detectable moiety is digoxigenin.

6. A method according to claim 4, wherein the detectable moiety is bromine.

7. A method according to claim 3, wherein the detectable moiety is a fluorophore.

8. A method according to claim 1, further comprising the steps of:
   contacting the tissue sample with a solution containing a protease; and
   washing the tissue sample to remove the protease.

9. A method according to claim 2, wherein the detecting step is performed using a reagent comprising an enzyme.

10. A method according to claim 9, wherein the enzyme is selected from the group consisting of phosphatases, galactosidases, glucuronidases, peroxidases and luciferases.

11. A method according to claim 10, wherein the enzyme is an alkaline phosphatase.

12. A method according to claim 10, wherein the enzyme is a β-galactosidase.

13. A method according to claim 10, wherein the enzyme is a glucuronidase.

14. A method according to claim 10, wherein the enzyme is a peroxidase.

15. A method according to claim 14, wherein the enzyme is horseradish peroxidase.

16. A method according to claim 10, wherein the enzyme is a luciferase.

17. A method according to claim 2, wherein the detecting step is performed using a reagent comprising an antibody or fragment thereof that binds to the detectable moiety.

18. A method according to claim 17, wherein the antibody or fragment thereof binds to digoxigenin.

19. A method according to claim 17, wherein the antibody or fragment thereof binds to bromine.

20. A method according to claim 2, further comprising the steps of:
   contacting the tissue sample with a reagent that comprises a first molecule that binds to the detectable moiety; and
   subsequently contacting the tissue sample with a reagent that comprises a second molecule that binds to the first molecule.

21. A method according to claim 20, wherein the first molecule is selected from the group consisting of antibodies, fragments of antibodies, avidin and streptavidin.

22. A method according to claim 21, wherein the second molecule comprises a signaling portion selected from the group consisting of phosphatases, galactosidases, glucuronidases, peroxidases, luciferases, chromophores, fluorophores, and radio-labeled materials.

23. A method according to claim 22, wherein the enzyme is an alkaline phosphatase.

24. A method according to claim 22, wherein the enzyme is a β-galactosidase.

25. A method according to claim 22, wherein the enzyme is a glucuronidase.

26. A method according to claim 22, wherein the enzyme is a peroxidase.

27. A method according to claim 26, wherein the enzyme is horseradish peroxidase.

28. A method according to claim 22, wherein the enzyme is a luciferase.

29. A method according to claim 2, further comprising the step of:

contacting the tissue sample with a reagent that comprises a molecule having a first portion that binds to the detectable moiety and a second portion that comprises an enzyme.

30. A method according to claim 29, wherein the first portion is selected from the group consisting of antibodies, fragments of antibodies, avidin and streptavidin.

31. A method according to claim 30, wherein the second portion comprises an enzyme selected from the group consisting of phosphatases, galactosidases, glucuronidases, peroxidases and luciferases.

32. A method according to claim 30, wherein the first portion is an antibody.

33. A method according to claim 32, wherein the second portion comprises an alkaline phosphatase.

34. A method according to claim 32, wherein the second portion is a β-galactosidase.

35. A method according to claim 32, wherein the second portion is a glucuronidase.

36. A method according to claim 32, wherein the second portion is a peroxidase.

37. A method according to claim 36, wherein the second portion is a horseradish peroxidase.

38. A method according to claim 32, wherein the second portion is a luciferase.

39. A method according to claim 30, wherein the first portion is a fragment of an antibody.

40. A method according to claim 39, wherein the second portion comprises an enzyme selected from the group consisting of phosphatases, galactosidases, glucuronidases, peroxidases and luciferases.

41. A method according to claim 39, wherein the second portion comprises an alkaline phosphatase.

42. A method according to claim 39, wherein the second portion comprises a β-galactosidase.

43. A method according to claim 39, wherein the second portion comprises a glucuronidase.

44. A method according to claim 39, wherein the second portion comprises a peroxidase.

45. A method according to claim 44, wherein the second portion is horseradish peroxidase.

46. A method according to claim 39, wherein the second portion is a luciferase.

47. A method according to claim 30, wherein the first portion comprises streptavidin and the second portion comprises an enzyme selected from the group consisting of phosphatases, gaiactosidases, glucuronidases, peroxidases, and luciferases.

48. A method according to claim 47, wherein the second portion comprises an alkaline phosphatase.

49. A method according to claim 47, wherein the second portion comprises a β-galactosidase.

50. A method according to claim 47, wherein the second portion comprises a glucuronidase.

51. A method according to claim 47, wherein the second portion comprises a peroxidase.

52. A method according to claim 51, wherein the second portion is horseradish peroxidase.

53. A method according to claim 47, wherein the second portion is a luciferase.

54. A method of detecting apoptotic cells in a sample, comprising the steps of:

isolating DNA from the sample;

fractionating the DNA by size;

transferring the DNA to a solid support;

contacting the solid support with a solution containing a nucleic acid probe molecule and a nucleic acid ligase enzyme, the nucleic acid molecule being ligatable to a 3'-overhang; and detecting the nucleic acid probe molecule, wherein the detection of the nucleic acid probe molecule correlates to the presence of apoptotic cells.

55. A method according to claim 54, wherein the nucleic acid probe molecule comprises a detectable moiety.

56. A method according to claim 55, wherein the detectable moiety is selected from the group consisting of enzymes, small molecules, chromophores, fluorophores, and radio-labeled materials.

57. A method according to claim 56, wherein the detectable moiety is a small molecule selected from the group consisting of digoxigenin, biotin, and bromine.

58. A method according to claim 57, wherein the detectable moiety is digoxigenin.

59. A method according to claim 57, wherein the detectable moiety is bromine.

60. A kit for the detection of apoptotic cells, comprising:

a nucleic acid molecule that can be ligated to a 3'-overhang, said nucleic acid molecule comprising a detectable moiety;

a nucleic acid ligase enzyme; and reagents for detecting the detectable moiety.

61. A kit according to claim 60, wherein said nucleic acid molecule is attached to a solid support.

62. A kit for simultaneously detecting apoptotic cells and proteins associated with the apoptotic cells, comprising;

a nucleic acid molecule that can be ligated to a 3'-overhang, said nucleic acid molecule comprising a first detectable moiety;

an antibody specific for a protein associated with apoptotic cells, said antibody comprising a second detectable moiety;

a nucleic acid ligase enzyme;

reagents for detecting the first detectable moiety;

reagents for detecting the second detectable moiety.

63. A kit for simultaneously detecting apoptotic cells and RNA molecules associated with the apoptotic cells, comprising:

a first nucleic acid molecule that can be ligated to a 3'-overhang, said first nucleic acid molecule comprising a first detectable moiety;

a second nucleic acid molecule that hybridizes to an RNA molecule associated with apoptotic cells, said second nucleic acid molecule comprising a second detectable moiety;

a nucleic acid ligase enzyme;

reagents for detecting the first detectable moiety;

reagents for detecting the second detectable moiety.

64. A method for the detection of proteins in apoptotic cells in a tissue sample, comprising the steps of:

fixing a tissue sample containing apoptotic cells;

heating the sample;

contacting the sample with a solution containing a first molecule that forms a complex with a protein in an apoptotic cell;

contacting the sample with a solution containing a second molecule that comprises a first detectable moiety and forms a specific complex with the first molecule;

contacting the sample with a solution that contains a nucleic acid molecule, the nucleic acid molecule having a second detectable moiety, and being ligatable to a 3'-overhang and a nucleic acid ligase enzyme; and detecting the complex and the nucleic acid molecule, wherein the detection of the complex in the same cell as the nucleic acid molecule correlates to the presence of the protein in apoptotic cells.

65. A method according to claim 64, wherein the first molecule is an antibody.

66. A method according to claim 65, wherein the second molecule comprises a first detectable moiety selected from the group consisting of enzymes, small molecules, chromophores, fluorophores, and radio-labeled materials.

67. A method according to claim 66, wherein the first detectable moiety is an enzyme selected from the group consisting of phosphatases, galactosidases, glucuronidases, peroxidases and luciferases.

68. A method according to claim 67, wherein the detectable moiety comprises an alkaline phosphatase.

69. A method according to claim 67, wherein the detectable moiety comprises a β-galactosidase.

70. A method according to claim 67, wherein the detectable moiety comprises a glucuronidase.

71. A method according to claim 67, wherein the detectable moiety is a peroxidase.

72. A method according to claim 71, wherein the detectable moiety comprises horseradish peroxidase.

73. A method according to claim 67, wherein the detectable moiety is a luciferase.

74. A method for the detection of RNA molecules in apoptotic cells in a tissue sample, comprising the steps of:

fixing a tissue sample containing apoptotic cells;

contacting the tissue sample with a solution containing a first nucleic acid molecule, the first nucleic acid molecule being capable of hybridizing with an RNA molecule present in apoptotic cells, the first nucleic acid molecule containing a first detectable moiety and being capable of being ligated to a 3'-overhang;

contacting the tissue sample with a solution containing a second nucleic acid molecule and a nucleic acid ligase enzyme, the second nucleic acid molecule comprising a second detectable moiety; and detecting the first nucleic acid molecule and the second nucleic acid molecule, wherein the detection of the first nucleic acid molecule in the same cell as the second nucleic acid molecule correlates to the presence of RNA molecules in apoptotic cells.

75. A method according to claim 74, wherein the first detectable moiety is selected from the group consisting of enzymes, small molecules, chromophores, fluorophores and radio-labeled molecules.

76. A method according to claim 75, wherein the second detectable moiety is selected from the group consisting of enzymes, small molecules, chromophores, fluorophores and radio-labeled molecules.

77. A method according to claim 76, wherein the first detectable moiety and the second detectable moiety are fluorophores.

78. A method for detecting the presence of apoptotic cells in a sample, comprising the steps of:

isolating DNA from a sample;

fixing a nucleic acid molecule to a solid support, the nucleic acid molecule being ligatable to a 3'-overhang;

ligating the DNA to the nucleic acid molecule; and detecting the ligation of the DNA to the nucleic acid, wherein the ligation of DNA to nucleic acid correlates to the presence of apoptotic cells in the sample.

79. A method according to claim 78, wherein the nucleic acid molecule includes a nucleotide sequence that serves as a recognition site for a restriction endonuclease.

80. A method according to claim 78, wherein the nucleic acid molecule is cleavably fixed to the solid support.

81. A method for detecting apoptotic cells in a sample, comprising the steps of:

isolating DNA from a sample;

fixing the DNA to a solid support;

contacting the solid support with a solution containing a nucleic acid molecule and a nucleic acid ligase enzyme, the nucleic acid molecule being ligatable to a 3'-overhang; and detecting the presence of the nucleic acid molecule, wherein the presence of the nucleic acid molecule correlates to the presence of apoptotic cells in the sample.

* * * * *